United States Patent [19]

Brodnick et al.

[11] Patent Number: 5,474,079
[45] Date of Patent: Dec. 12, 1995

[54] SIGNAL ACQUISITION METHOD

[75] Inventors: Donald E. Brodnick, Cedarburg; David G. Hernke, Sussex, both of Wis.

[73] Assignee: Marquette Electronics, Inc., Milwaukee, Wis.

[21] Appl. No.: 204,751

[22] Filed: Mar. 2, 1994

[51] Int. Cl.⁶ ............................................. A61B 5/0432
[52] U.S. Cl. ............................................. 128/711
[58] Field of Search ................................. 128/702, 704, 128/711

[56] References Cited

U.S. PATENT DOCUMENTS

| | | | |
|---|---|---|---|
| 4,006,737 | 2/1977 | Cherry | 128/2.06 |
| 4,073,011 | 2/1978 | Cherry et al. | 364/900 |
| 4,240,442 | 12/1980 | Andresen et al. | 128/708 |
| 4,316,249 | 2/1982 | Gallant et al. | 364/417 |
| 4,696,306 | 9/1987 | Shiozaki | 128/711 |
| 4,989,610 | 2/1991 | Patton et al. | 128/695 |
| 5,240,009 | 8/1993 | Williams | 128/702 |
| 5,318,036 | 7/1994 | Arand et al. | 128/696 |

OTHER PUBLICATIONS

R. Vincent Ditayler, "Artefactual ST segment abnormalities due to electrocardiograph design", Br Heart, vol. 54, 1985, pp. 121–128.

Donald E. Brodnick and Marilyn M. Johnson, paper entitled "Holter Hookup: The 12 Lead Challenge", May 14, 1991.

James J. Bailey, MD, et al., "Recommendations for Standardization and Specifications in Automated Electrocardiography: Bandwidth and Digital Signal Processing", Special Report Circulation, vol. 81, No. 2, pp. 730–739, Feb. 1990.

Primary Examiner—William E. Kamm
Attorney, Agent, or Firm—Michael, Best & Friedrich

[57] ABSTRACT

A signal acquisition method comprises the steps of recording ECG data signals on a tape in a first direction through a first high pass filter; and acquiring the data from the tape in an analyzer in a reverse direction through a second high pass filter having the same effective characteristics as the first filter.

12 Claims, 1 Drawing Sheet

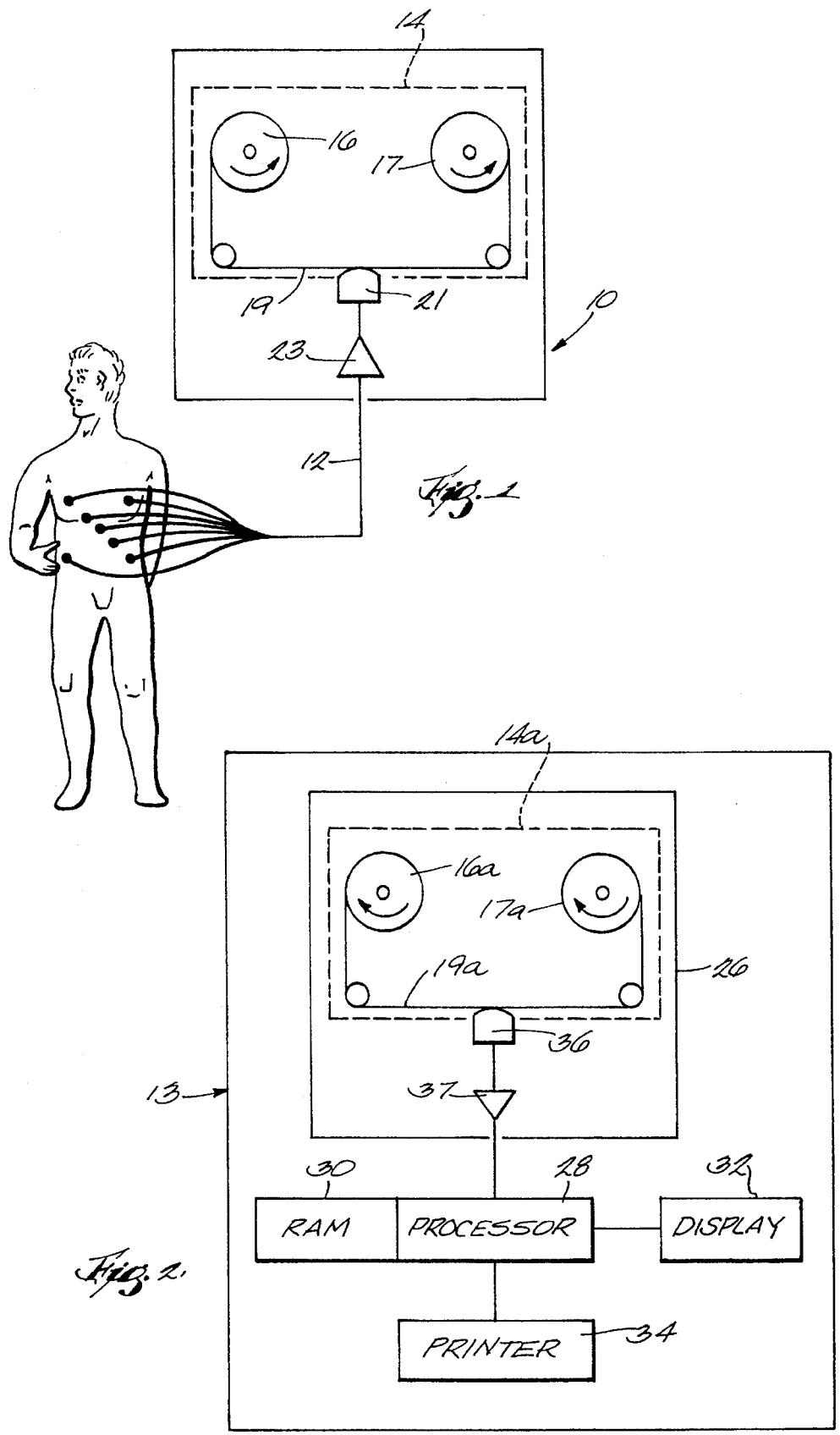

SIGNAL ACQUISITION METHOD

BACKGROUND OF THE INVENTION

This invention relates to signal acquisition and more particularly to acquisition of electrocardiograms.

Surface electrocardiograms are derived from electrical activity of nerves and muscles of the heart which extend to the surface of the skin. To obtain ECG signals, three or more electrodes are connected to selected locations on the patient's body. Pairs of patient electrodes are connected to differential amplifiers to provide one or more channels of ECG "leads" which are wave forms depicting electrical activity of the heart viewed along specific axes. An additional electrode is required to eliminate the common mode voltage which exists between the patient and the recording instrumentation and is common to all of the ECG signals.

Cardiac disorders that can be identified by electrocardiograms are either transient or persistent. Resting ECG's, which are performed in a doctor's office or a hospital, can detect persistent disorders which are identifiable in almost every heart beat if viewed at the correct angle. In order to determine the cause of transient disorders that occur rarely or cannot be reproduced in the doctor's office, such as ischemia and arrhythmia, ECG signals must be recorded for longer periods, typically 24 hours. In the event it is desired to obtain such signals while the patient performs his or her routine activities, the patient is connected to a portable ECG recorder commonly called an ambulatory or Holter monitor.

An ECG is a complex signal of irregular shape consisting of P, QRS and T complexes. The portion between the S and T complexes is called the ST segment. Deviations in the shape and rhythm of the ECG wave form from established norms are an indication of various cardiac abnormalities. For example, elevation or depression of the ST segment is an indication of ischemia, or an insufficiency in the supply of oxygen to the cardiac muscle.

ECG signals are often contaminated with electrical noise, some of which are external, such as power line interference. Other noise signals are caused by the patient. For example, such activity as the movement of skeletal muscles cause a high frequency noise signal. In addition, low frequency noise signals typically result from patient respiration or the slowly changing potentials caused by the electrode skin interface. These low frequency noise signals are often referred to as base line sway and generally occur at less than one Hz in the signal frequency spectrum.

If the ECG signal is to be recorded without distortion, the recording equipment must have an unvarying or flat amplitude response over the range of frequencies present in the signal. In addition, the system must have a linear phase response over the required frequency range so that all components passing through the recorder are delayed by the same amount. If the phase response is non-linear, components of the P, QRS and T complexes are delayed selectively and distortion will result.

In order to provide sufficient data for diagnosis, Holter monitors normally record several channels of ECG data, each of which is a view of the heart along a different axis. However, if base line sway, caused by low frequency noise signals, is permitted to occur, the various printed ECG signals become difficult to interpret if displacement of the signals in the different recording channels interfere one with the other. Therefore, Holter recorders generally include high pass filters to remove low frequency signals which cause base line sway. However, the use of such high pass filters to correct for base line drift tend to cause the ST segment of the ECG signal to be displaced in a direction opposite that of the QRS complex. This can cause the ST segment to be distorted so that an incorrect reading of the ST segment elevation may result.

SUMMARY OF THE INVENTION

It is an object of the invention to provide a new and improved method for the acquisition of pre-recorded signals.

Another object of the invention is to provide a new and improved method for the acquisition of pre-recorded signals which improves base line correction.

A further object of the invention is to provide a new and improved method of acquiring prerecorded ECG signals which minimizes base line sway.

Yet another object of the invention is to provide a method for the acquisition of pre-recorded signals which preserves linear phase response.

A still further object of the invention is to provide a method and apparatus for acquiring pre-recorded signals wherein acquisition time is reduced.

It is another object of the invention to provide a new and improved method of acquiring prerecorded ECG signals wherein phase distortion is substantially eliminated.

These and other objects and advantages of the invention will become more apparent from the detailed description thereof taken with the accompanying drawings.

These objects are obtained by recording the ECG signals through a first high pass filtering means and then acquiring the recorded data in a reverse direction through a second high pass filtering means having the same effective filtering characteristics as the first. The first high pass filtering means removes low frequency noise signals so as to reduce base line drift. However, the first high pass filtering means introduces a predictable phase distortion into the recorded signal. Acquiring the recorded data in a reverse direction through a second high pass filtering means acts to further move the signal toward the center of the viewing channel. In addition, because the ECG signal is filtered in the reverse direction through a second high pass filtering means having the same effective filtering characteristics as the first, all phase distortion introduced by the first filtering means are reversed by the second. As a result, a more accurate representation of the contour of the P, QRS and T complexes is obtained while the effect of low frequency noise signals is substantially eliminated.

BRIEF DESCRIPTION OF THE DRAWINGS

FIG. 1 schematically illustrates a Holter monitor; and

FIG. 2 schematically illustrates an analyzer for performing the method according to the invention.

DETAILED DESCRIPTION OF THE PREFERRED EMBODIMENT

FIG. 1 schematically illustrates an ambulatory or Holter monitor 10 coupled to a patient by leads 12 and FIG. 2 schematically illustrates a diagnostic system 13. A tape cassette 14 is shown to be disposed within the Holter monitor 10 and includes a supply reel 16 and a take up real 17 for a magnetic tape 19. The reels 16 and 17 are driven in the forward direction, shown by the counter clockwise arrows, by a conventional motor drive (not shown) and which is a component part of the Holter monitor 10.

As those skilled in the art will appreciate, the Holter monitor 10 also includes a recording head 21. A high pass filtering means 23 is connected between the patient cable 12 and the recording head 21. The ECG signals are thus high pass filtered before recording for the removal of low frequency noise. In the preferred embodiment, the tape 19 includes four channels of which three are for recording ECG signals and the fourth is for the clock signal. While in the preferred embodiment the ECG data is recorded on magnetic tape, it could also be recorded on some other medium such as a diskette.

The analysis system 13 includes a playback assembly 26, a processor 28 having a random access memory (RAM) 30, a display 32, and a printer 34, all of which are well known in the art. The tape player 26 is also shown to contain a cassette 14a having a tape 19a. Those skilled in the art will appreciate that the tape 19a is one on which ECG signals were previously recorded on a Holter monitor such as that shown in FIG. 1. Moreover, when placed in the player 26, that portion of the tape 19a which contains the ECG signals is disposed on the take up reel 17a. The playback assembly 26 is constructed and arranged to play the tape in the reverse direction from the take up reel 17a to the supply reel 16a is shown by the clockwise arrows in FIG. 2. The playback assembly 26 also includes a playback head 36 and high pass filtering means 37 which is schematically illustrated as a single filter. However, it will be appreciated that the high pass filtering means 37 is the total effective filter acting on the signal as it passes from the tape 19a to the analysis system 13 including any hardware or software filters in the playback head or the analysis system itself. The important characteristic of the filtering means 37 is that it eliminates any phase distortion in the signal that is introduced by the first filtering means 23. Moreover, the filtering means 23 and 37 may be analog or digital filters.

The filtered ECG signals from the recording head 36 are passed to the RAM 30 for storage. In the recording operation, the monitor 10 is connected to the patient by cable 12 so that the ECG lead signals are generated and recorded. Recording proceeds in the conventional manner from the commencement of the ECG signals and continues until the recording period is completed and recording of the signals is terminated. In the acquisition step, the tape is moved past the play back head 36 in the reverse direction from which it was recorded, that is, from the termination of the date to its commencement. If the data is recorded on a diskette or a solid state memory instead of a tape, the data would likewise be acquired commencing at the terminal portion and continuing in the reverse direction to the initial portion.

After acquisition, the data can be analyzed by the processor 28 in either the forward or reverse direction for rhythm and contour irregularities in the ECG signals. These signals may also be displayed fully on the display 32 or segments of the recorded data can be displayed to show irregularities in particular beats. The data may also be printed on a paper strip by the printer 34. Such displays or printouts may be in either the forward or reverse direction. It will also be appreciated that the processor 28 may include buffers.

The recording high pass filtering means 23 and the playback high pass filtering means 37 preferably have the same filtering characteristics, taking into consideration the difference in recording and playback speeds. For example, if the cut-off frequency of filtering means 23 is 0.3 Hertz and the recording speed of the Holter monitor 10 is 1 mm/sec and the playback speed of the player 26 is 1,000 mm/sec., the cut-off frequency of filtering means 37 is preferably 300 Hertz.

By acquiring the data from the tape 19a through the filtering means 37 in the reverse direction, any phase distortion in the ECG signal caused by the high pass filtering means 23 is reversed by the filtering means 37 because the data is acquired in the reverse direction. This provides increased baseline correction and preserves linear phase response. Therefore, the processor 28 can make an analysis of ECG signals which are free of phase distortion. Moreover, because the tape 19b does not have to be rewound before the data is acquired by the RAM 30, significant time is saved in the analysis and display of the ECG wave forms.

While the invention has been illustrated and described in connection with the recording and analyzing of ECG data signals, it also has application to other systems where data is recorded through a filtering system which is likely to cause distortion. Therefore, while only a single embodiment of the invention has been illustrated and described, is not intended to be limited thereby but only by the scope of the appended claims.

I claim:

1. A method of recording data signals from a source of said signals on a recording medium and acquiring the data signals from said medium for analysis, said data signals having a commencement and a termination, and including the steps of providing a first filtering means, filtering said data signals through the first filtering means, recording the filtered data signals on a recording medium continuously from the commencement to the termination thereof, providing a second filtering means having the same characteristics as the first filtering means, acquiring the data signals from the recording medium after completion of the recording step and in the reverse direction from that in which the data signals were recorded beginning at the termination and continuing without interruption to the commencement, filtering the reverse data signals through the second filtering means as it is being acquired from the recording medium, whereby phase distortion introduced into said data signals by said first filtering means are canceled by the second filtering means.

2. The method set forth in claim 1 wherein said data signals consist of ECG signals, wherein said filtering steps comprise first high pass filtering of said ECG data signals prior to the recording thereof and second high pass filtering said data signals as they are acquired in the reverse direction the duration of said signals from commencement to termination being greater than an hour.

3. The method set forth in claim 1 wherein the filtering steps comprise first high pass filtering said data prior to the recording thereof and second high pass filtering the recorded data during the acquisition thereof and including the step of compensating during the second high pass filtering step for any phase distortion introduced during the first high pass filtering step.

4. The method set forth in claim 1 wherein said filtering steps comprise filtering said ECG signals prior to recording through a first high pass filtering means and filtering the recorded signals as they are acquired through a second high pass filtering means having the same effective characteristics as the first high pass filtering means so that distortion introduced into said ECG signals by said first high pass filtering means is compensated by said second high pass filtering means.

5. A method of recording ECG data signals from a patient on a recording medium and acquiring the signals from the recording medium for analysis, comprising the steps of filtering ECG data signals having a beginning and an end through a first filtering means and recording the same on the recording medium commencing at the beginning of said ECG data signals and continuing without interruption until the end thereof, acquiring the ECG data signals from the recording medium in an ECG analyzer after the completion of the recording step commencing at the end of said data signals and continuing without interruption until the beginning thereof, and filtering the ECG data signals prior to acquisition through a second filtering means having the same characteristics as the first filtering means to compensate for phase distortion introduced by said first filtering means, and analyzing the ECG data signals for contour irregularities.

6. A method of recording and analyzing ECG data signals acquired from a patient for contour or rhythm irregularities, the steps of, filtering low frequency components of said ECG data signals whereby phase distortion is introduced into said ECG data signals, recording the filtered ECG data signals in a first direction on a recording medium from the commencement of said signals to the termination thereof, acquiring the ECG data signals from the recording medium in the reverse direction without interruption and from the termination to the commencement thereof, filtering low frequency components of said data signals as the data is acquired in the reverse direction to compensate for the phase distortion introduced during recording, and analyzing the ECG data signals for contour or rhythm irregularities.

7. The method set forth in claim 6 wherein said filtering steps comprise filtering said ECG data signals prior to recording through a first high pass filtering means having predetermined filtering characteristics and filtering the recorded signals as they are acquired through a second high pass filtering means having the same effective characteristics as the first high pass filtering means so that distortion introduced into said ECG data signals by the first high pass filtering means is compensated by the second high pass filtering means.

8. The method set forth in claim 7 wherein the duration of the step of recording the ECG signals from a patient continues for a period of a plurality of hours.

9. A method of recording ECG data signals from a source of said signals on a recording medium and acquiring the data from said medium for analysis, said data signals having a commencement and a termination, and including the steps of providing a first high pass filtering means, filtering said data signals through the first high pass filtering means, recording the filtered data signals on a recording medium at a first linear speed from the commencement to the termination thereof, acquiring the data signals from the recording medium at a second linear speed higher than the first linear speed and in the reverse direction from that in which the same was recorded beginning at the termination and continuing to the commencement, providing a second high pass filtering means, high pass filtering the reverse data signals through the second high pass filtering means, selecting the second high pass filtering means such that it has the same effective characteristics as the first high pass filtering means and with a cutoff frequency equal to that of the first high pass filtering means times the ratio of the acquisition speed over the recording speed, whereby phase distortion introduced into said data signals by said first high pass filtering means are canceled.

10. A method of recording ECG signals from a patient on magnetic tape and acquiring the signals from the magnetic tape for analysis, comprising the steps of filtering ECG signals having a beginning and an end through a first filtering means, moving the tape in a first direction past a recording head for recording said filtered ECG signals on the tape commencing with the beginning of the ECG signals and continuing to record until the end of the ECG signals, acquiring the ECG signals from the tape in an ECG analyzer commencing at the end of the ECG signals and continuing until the beginning thereof, and filtering the ECG signals prior to acquisition through a second filtering means having the same characteristics as the first filtering means to compensate for phase distortion introduced by the first filtering means, and analyzing the ECG signals for contour irregularities.

11. The method set forth in claim 10 and including the steps of moving the tape in a first direction past the recording head during the recording of said ECG signals and wherein the acquiring step comprises moving the tape past a playback head in the opposite direction during the acquisition of said ECG signals.

12. A method of recording ECG signals from a patient on a recording medium and acquiring the signals from the recording medium for analysis, comprising the steps of filtering ECG signals having a beginning and an end through a first filtering means, moving the recording medium in a first direction past a recording head for recording the ECG signals on the recording medium commencing at the beginning of said ECG signals and continuing until the end thereof, moving the medium past a playback head in the opposite direction for acquiring the ECG signals from the recording medium in an ECG analyzer commencing at the end of the ECG signals and continuing until the beginning thereof, and filtering the ECG signals prior to acquisition through a second filtering means having the same characteristics as the first filtering means to compensate for phase distortion introduced by the first filtering means, and analyzing the ECG signals for contour irregularities.

* * * * *